(12) United States Patent
Siviero et al.

(10) Patent No.: US 6,458,558 B1
(45) Date of Patent: Oct. 1, 2002

(54) PROCESS FOR THE PREPARATION OF β-LACTAM DERIVATIVES

(75) Inventors: Enrico Siviero, Pavia; Walter Cabri, Rozzano; Daniele Mario Terrassan, Concorezzo, all of (IT)

(73) Assignee: Antibioticos S.p.A., Rodano (IT)

( * ) Notice: Subject to any disclaimer, the term of this patent is extended or adjusted under 35 U.S.C. 154(b) by 0 days.

(21) Appl. No.: 09/979,164

(22) PCT Filed: May 16, 2000

(86) PCT No.: PCT/EP00/04372

§ 371 (c)(1),
(2), (4) Date: Feb. 11, 2002

§ 102(e) Date: Feb. 11, 2002

(87) PCT Pub. No.: WO00/71547

PCT Pub. Date: Nov. 30, 2000

(30) Foreign Application Priority Data

May 21, 1999 (IT) .......................... MI99A1120

(51) Int. Cl.$^7$ .......................... C12P 35/00; C12P 35/02; C07D 501/34; C07D 501/00
(52) U.S. Cl. .......................... 435/47; 435/51; 540/215; 540/230
(58) Field of Search ...................... 435/47, 51; 540/230

(56) References Cited

U.S. PATENT DOCUMENTS 5,354,667 A    10/1994  Croux et al.
5,424,196 A    6/1995   Cambiaghi et al.
5,801,241 A    9/1998   Lim et al.

FOREIGN PATENT DOCUMENTS

WO    WO 98/43980    10/1998

OTHER PUBLICATIONS

Nobufusa Serizzawa et al.: "Enzymatic conversion of cephamycin by D–amino acid oxidase from trigonolsis variabilis" Journal of Antibiotics., vol. 33, No. 6, 1080, pp. 585–590, XP002147054 Japan Antibiotics Research Association. Tokyo., JP, ISSN: 0021–8820 the whole document.

*Primary Examiner*—Herbert J. Lilling
(74) *Attorney, Agent, or Firm*—Arent Fox Kintner Plotkin & Kahn

(57) ABSTRACT

A process for the preparation of Cefuroxime acid (I), which comprises the following steps: (1) Extraction of deacetyl 7-glutaryl ACA (II) aqueous solution at acid pH with organic solvents (for example according to the procedures disclosed in U.S. Pat. No. 5,801,241); (2) drying the resulting solution while preventing lactonization of the intermediate; (3) carbamoylation of the hydroxymethyl group at the 3-position by reaction with chlorosulfonyl isocyanate or similar products; (7) extraction of the carbamoyl derivative from step 3 with water at neutral pH; (8) enzymatic hydrolysis of the amide at the 7-position of the cephalosporanic ring with glutaryl acylase; (6) acylation of the amnino group by condensation with 2-furanyl(sin-methoxyimino)acetic acid chloride or mixed anhydride.

8 Claims, No Drawings

PROCESS FOR THE PREPARATION OF β-LACTAM DERIVATIVES

CROSS-REFERENCE TO RELATED APPLICATION

This application is a National Stage entry of International Application No. PCT/EP00/04372, filed May 16, 2000, the entire specification claims and drawings of which are incorporated herewith by reference.

The present invention generally relates to the field of organic chemistry.

More particularly, the invention relates to a process for the preparation of Cefuroxime acid, i.e. (6R,7R)-7-[[2-furanyl (sin-methoxyimino)acetyl]amino]-3-carbamoyloxymethylceph-3-em-4-carboxylic) acid, and the salts thereof, starting from (6R,7R)-7-[(4-carboxy-1-oxobutyl)amino]-3-hydroxymethyl-ceph-3-em-4-carboxylic acid (deacetyl 7-glutaryl ACA).

Cefuroxime acid is a key intermediate for the industrial synthesis of two third generation cephalosporins, Cefuroxime sodium (for the injection administration) and Cefuroxime Axetil (for the oral administration). These molecules are therapeutically valuable thanks to their effective broad spectrum antibacterial activity against gram-negative bacterials, in particular in the treatment of immunodepressed patients. Their effectiveness is advantageously combined with remarkable resistance to βlactamases.

The synthesis of Cefuroxime disclosed in U.S. Pat. No. 3,966,717 and U.S. Pat. No. 3,974,153 comprises 8 synthetic steps starting from 7-ACA (7-amino cephalosporanic acid). Such high number of steps, which causes a low overall yield, is due to the introduction of two protective groups, the first (e.g. thienyl acetyl) on the amine function and the second (e.g. benzhydryl) on the 7-ACA acid function.

Subsequently, processes starting from 7-ACA have been developed (Wilson, E.M. Chemistry and Industry 1984, 217) which do not involve the use of protective groups and remarkably reduce the number of steps. In particular, the best process, illustrated in Scheme 1, comprises 3 steps:

1. Conversion of 7-ACA into deacetyl-7-ACA;
2. Acylation of the amino group;
3. Carbamoylation of the C-3 alcohol group (Scheme 1).

SCHEME 1

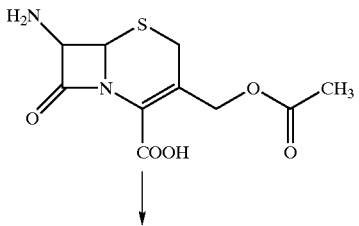

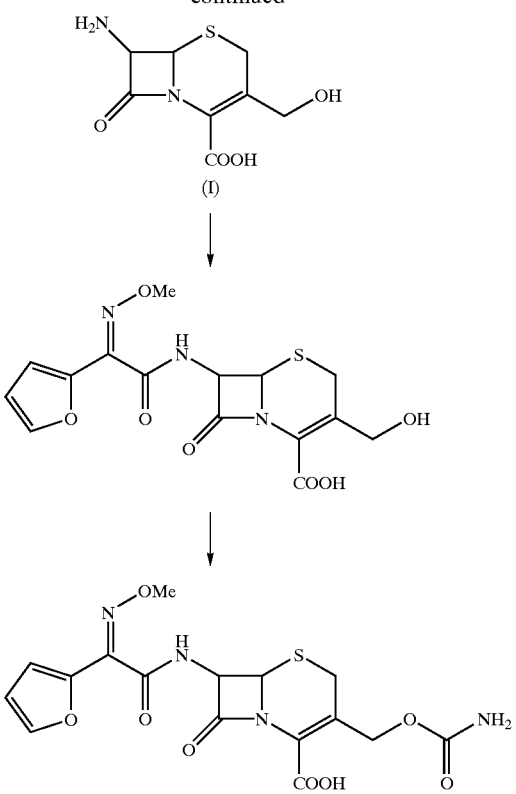

It has now surprisingly been found that Cefuroxime can be prepared starting from intermediates of 7-ACA enzymatic synthesis without isolating any intermediate.

The enzymatic synthesis of 7-ACA involves, depending on the used process, an intermediate that can either be glutaryl-7-ACA (U.S. Pat. No. 5,424,196; Bianchi, D., Bortolo, R., Golini, P., Cesti, P. La Chimica e l'Industria 1998, 80, 879), which can be enzymatically converted into deacetyl 7-glutaryl ACA (II), or (II) itself, from fermentative processes yielding des-Cephalosporin C (U.S. Pat. No. 4,533,632).

The process object of this invention, illustrated in Scheme 2, comprises the following steps:

1. Extraction of deacetyl 7-glutaryl ACA (II) aqueous solution at acid pH with organic solvents (for example according to the procedures disclosed in U.S. Pat. No. 5,801,241).

2. Drying the resulting solution while preventing lactonization of the intermediate.

3. Carbamoylation of the hydroxymethyl group at the 3-position by reaction with chlorosulfonyl isocyanate or similar products.

4. Extraction of the carbamoyl derivative from step 3 with water at neutral pH.

5. Enzymatic hydrolysis of the amide at the 7-position of the cephalosporanic ring with glutaryl acylase.

6. Acylation of the amino group by condensation with 2-furanyl(sin-methoxyimino)acetic acid chloride or mixed anhydride.

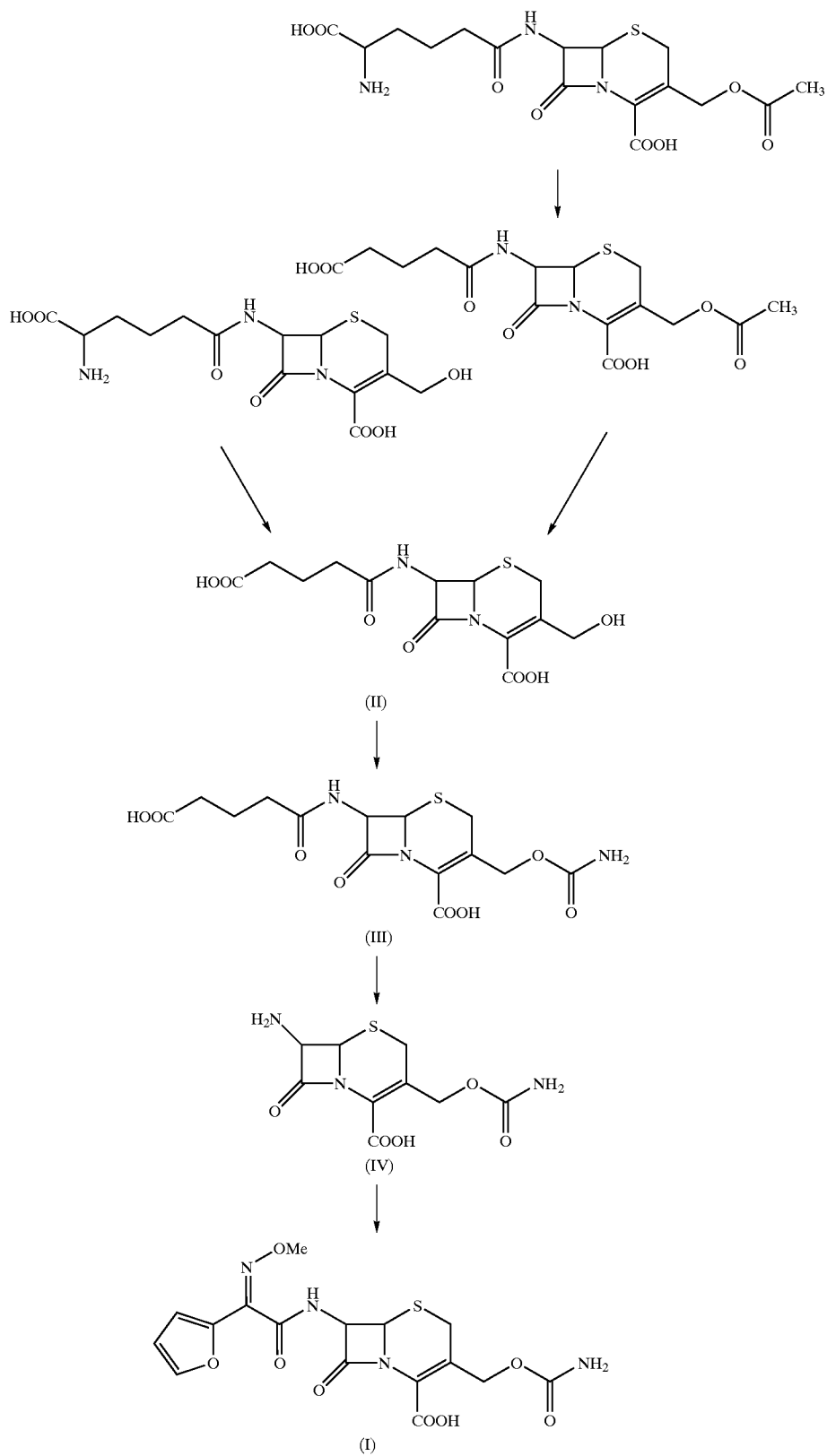

The process of the invention involves a reduction of the number of the steps compared with the known processes for the preparation of Cefuroxime, as it requires neither the protection of the carboxyl at the 4-position of the cephalosporanic ring nor that of the amino group at the 7-position nor the recovery of any intermediates, thus causing a remarkable increase in the overall yield directly starting from des-Cephalosporin C or Cephalosporin C fermentation broth after enzymatic deacetylation.

Furthermore, the process of the invention allows making use of intermediates, which, contrary to 7-ACA, are particularly stable in aqueous solution.

The process according to the present invention provides Cefuroxime acid or a salt thereof which can be transformed into the corresponding commercial products Cefuroxime sodium and Cefuroxime axetil.

The process described above comprises the preparation of an intermediate, which has to day never been described, namely (6R,7R)-7-[(4-carboxy-1-oxobutyl)amino]-3-carbamoyloxy-methyl-ceph-3-em-4-carboxylic acid of formula (III)

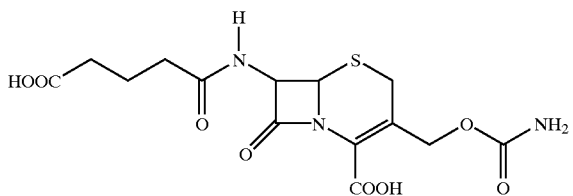

(III)

or a salt thereof.

The steps of the process according to the present invention for the preparation of Cefuroxime acid starting from deacetyl 7-glutaryl ACA (II) are described in detail hereinbelow.

1. Extraction of a deacetyl 7-glutaryl ACA (II) aqueous solution with an organic solvent, preferably cyclohexanone (U.S. Pat. No. 5,801,241).

A deacetyl 7-glutaryl ACA aqueous solution, at a concentration ranging from 1 to 20%, is adjusted to pH ranging from 1.0 to 3.0, preferably 1.5, at temperatures ranging from 0 to 15° C., preferably from 0 to 5° C. These conditions prevent degradation of the substrate to give a lactone following condensation of the carboxyl at the 4-position with the hydroxyl bound to the methyl at the 3-position. The resulting solution is added with 0.5 to 2 volumes of an organic solvent, preferably cyclohexanone, and extraction is carried out at temperatures ranging from 0 to 5° C. Phase are separated, then the aqueous phase is back-extracted with 0.5÷1.0 volumes of solvent and the organic phases are combined.

2. The resulting organic solution is brought to temperatures from 0 to 15° C., preferably from 0 to 5° C., adjusted to apparent pH ranging from 6 to 8, preferably 7, with a solution of triethylamine in the organic solvent used for the extraction. The resulting mixture is concentrated in vacuo and at a temperature below 25° C., to obtain a suspension with a water content below 0.5%, which is then processed in the subsequent step.

3. Conversion of deacetyl 7-glutaryl ACA (II) into the corresponding 3-carbamoyloxymethyl derivative (III), by reaction in cyclohexanone with an activated isocyanate, preferably chlorosulfonyl isocyanate. The suspension isolated at the end of the previous step, having a concentration ranging from 1 to 10%, is cooled to temperatures ranging from −30 to 0° C., preferably −10° C., and added, in small portions, with 1÷5 mols of chlorosulfonyl isocyanate per mol of substrate. The resulting heterogeneous mixture is then kept at such temperature until completion of the reaction, whose progression is monitored by HPLC chromatography.

4. Extraction of the carbamoyl derivative obtained in step 3. The solution from step 3 is added with 0.1÷0.3 volumes of cold water and the resulting heterogeneous mixture is then adjusted to pH ranging from 6 to 8, preferably 7, at temperatures ranging from 0 to 15° C., preferably from 0 to 5° C., with an aqueous ammonia solution. The two phases are separated; the organic phase is back-extracted with water, to 0.2 volumes; the aqueous phases are combined and the resulting solution, having a concentration ranging from 5 to 30%, is processed in the subsequent step.

5. Conversion of the 7-glutaryl 3-carbamoyloxymethyl derivative (III) into the corresponding 7-β-amino derivative (IV) by enzymatic hydrolysis of the amide at the 7-position of the cephalosporanic ring with glutaryl acylase. The resulting solution from the previous step is added with a glutaryl acylase isolated from an *Escherichia Coli* culture, suitably supported on a macroreticular resin, preferably polyacrylic epoxide, and the resulting suspension is kept at pH 7.0–9.0, preferably 7.5, at temperatures ranging from 20 to 30° C., preferably 25° C., until completion of the reaction. The progression of the hydrolysis of the glutaryl derivative to the corresponding cephalosporanic ring is monitored by HPLC chromatography. The reaction yield is higher than 85%. After completion of the reaction, the enzyme is removed and the product is converted into Cefuroxime acid.

6. (6R,7R)-7-Amino-3-carbamoyloxymethylceph-3-em-4-carboxylic acid (IV) is directly converted into Cefuroxime acid (I), adding the aqueous solution with a concentrated methylene chloride solution of 2-furanyl(sin-methoxyimino)-acetic acid chloride or mixed anhydride (preferably the chloride).

Optionally, intermediate (IV) can be recovered by acidification to isoelectric pH of the solution from the previous step, then be worked in the acylation of the amino group at the 7-position of the cephalosporanic ring, by following the method described in example 2 of U.S. Pat. No. 3,974,153.

EXAMPLE 1

300 ml of a 6% deacetyl 7-glutaryl ACA aqueous solution, cooled to 0÷5° C., is added with the necessary amount of sulfuric acid to adjust pH to 1.5. The resulting solution is extracted with one volume of cyclohexanone. The organic phase, kept at a 0÷5° C., is added with the triethylamine amount necessary to adjust pH to 6.0. The solution is then concentrated to water content below 0.5. At the end of the operation, 350 ml of a glutaryl deacetyl 7-ACA suspension containing 98% of the activity present in the solution resulting from extraction at acid pH, are obtained. The resulting solution is then transformed in the subsequent step.

EXAMPLE 2

The mixture from the previous step is cooled to −10IC and then added with 13 ml of chlorosulfonyl isocyanate, preventing temperature from exceeding −10° C. After completion of the addition of the reactive, the mixture is kept at −10° C. until the starting product disappears. At the end of the synthesis, the reaction yield is checked to be about 95%. 150 ml of cold water are added. The heterogeneous mixture is kept at a 0÷5° and its pH is adjusted with a 10% sodium carbonate solution. The two phases are separated, the organic phase is back-extracted with 50 ml of water. The resulting solution is then worked in the subsequent step.

The product from the above step was recovered adjusting to pH=2 the final aqueous solution saturated with sodium chloride. The isolated recovered was then characterized by analysis of the data from spectra Mass and NMR spectrometry.

$^1$H-NMR: 1.82 ppm, qui, J=7 Hz, 2H, side chain $CH_2$; 2.3 ppm, m, 4H, side chain methylenes; AB system at 3.4 ppm, methylene at the 2-position; system at 2.3 ppm, methylene bound to the oxygen; 5.05 ppm, d, J=5 Hz, 1H, H-6; 5.55 ppm, d, J=5 Hz, 1H, H-7. $^{13}$C-NMR: 22.81 ppm ($CH_2$); 25.92 ppm ($CH_2$); 35.61 ppm ($CH_2$); 36.99 ppm ($CH_2$); 57.98 ppm (CH); 58.90 ppm (CH); 65.84 ppm ($CH_2$—OR); 117.14 ppm (C-2); 132.04 ppm (C-3); 154.69 ppm (—OCON—); 165.78 ppm (two amide C=O); 169.30 ppm (COO—); 177.73 ppm (COOH). Electrospray ESI: m/z 388; m/z 410; m/z 344; m/z 327; m/z 349; m/z 309; m/z 299; m/z 281; m/z 253; m/z 185; m/z 172. Desadsorption chemical ionization (DCI): m/z 233; m/z 214; m/z 216

EXAMPLE 3

The resulting aqueous solution is diluted with 300 ml of water and added with 40 g of glutaryl 7-ACA acylase, whose preparation is described in example 12 of U.S. Pat. No. 5,424,196. The heterogeneous mixture stirred at 20° C. until completion of the reaction, automatically adjusting pH to 7.5 with 5% ammonia. The maximum conversion takes place after 60', when the solution yield is about 86%. The enzyme is removed and the resulting solution is processed in the subsequent step.

EXAMPLE 4

A mixture of phosphorous pentachloride (10 g) and methylene chloride (100 ml), in a reactor of suitable volume, cooled at 0° C., is added with 18.4 ml of N,N-dimethylacetamide. The resulting solution is cooled, added with of 8.5 g of 2-furanyl(sin-methoxyimino)acetic acid and stirred at −10° C. for 15'; 22 ml of cold water are added thereto, keeping the resulting heterogeneous mixture stirred, the two phases are separated and the organic phase is slowly added to the solution of the substrate isolated in the previous step (example 3), suitably cooled, automatically adjusting pH with 10% sodium hydroxide. The resulting mixture is kept at 0° C. until the substrate disappears. The final mixture is added with 50 ml of N,N-dimethylacetamide, 50 ml of acetonitrile and 300 ml of water, pH is adjusted to 2 with 2N hydrochloric acid and the resulting mixture is stirred at 0÷5° C. for one hour, filtered, washed with water, and dried under-vacuum at 30÷35° C. for 8 hours. 15 g of Cefuroxime acid are obtained in an 85% yield.

EXAMPLE 5

The product from the step described in example 3 is isolated by adjusting to the isoelectric pH the aqueous solution obtained at the end of this step.

A mixture of 8.4 g of said product, i.e. of (6R, 7R)-7-amino-3-carbomoiloxymethylceph-3-em-4-carboxylic (IV) acid, 37 ml of N,N-dimethylacetamide, 37 ml of acetonitrile, 21 ml of triethylamine and 5 ml of water is stirred at 0÷2° C. until complete dissolution of the product. Separately, a suspension of 7.7 g of phosphorous pentachloride in 75 ml of methylene chloride is added at 0÷2° C. with 14.2 ml of N,N-dimethylacetamide and the resulting solution is added at −10° C. with 6.5 g of 2-furanyl(sin-methoxyimino)acetic acid; the resulting solution is added with 17 ml of cold water, keeping the mixture at 0÷2° C. for about 15'. After that, the two phases are separated and the organic phase is added to the substrate solution prepared above, suitably cooled at −5° C. The reaction mixture is kept at 5÷10° C. until the substrate disappears. The final mixture is added at 0÷5° C. to a mixture of 570 ml of water and 50 ml of 2N hydrochloric acid, pH is adjusted to=2 with 2N hydrochloric acid and the resulting mixture is stirred at 0÷5° C. for about an hour, then filtered, washed with water and dried at 30÷35° C. for 8 hours. 11 g, of Cefuroxime acid are obtained in an 86% yield.

What is claimed is:
1. A process for the preparation of Cefuroxime acid (I)

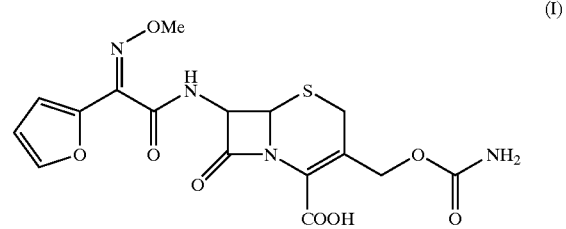

starting from deacetyl 7-glutaryl ACA (II), which comprises the following steps, without recovery of any intermediates:
   a) extracting a deacetyl 7-glutaryl ACA (II) aqueous solution at pH 1–3 and at a temperature of 0–15° C. with an organic solvent, to obtain an organic phase containing deacetyl 7-glutaryl ACA (II)

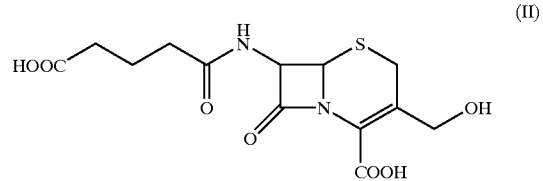

b) adjusting said organic phase to pH 6–8, then drying such phase by distillation under vacuum at a temperature below or equal to 25° C.;
   c) reacting deacetyl 7-glutaryl ACA (II) with an activated isocyanate at temperatures ranging from −30 to 0° C., to obtain (6R,7R)-7-[(4-carboxy-1-oxobutyl)amino]-3-carbamoyloxymethyl-ceph-3-em-4-carboxylic acid (III)

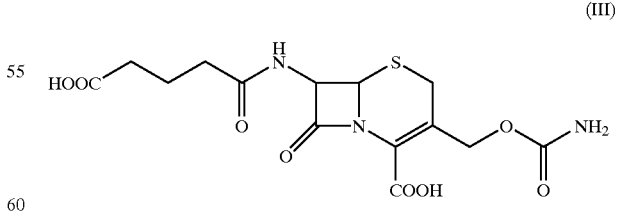

d) extracting said compound (III) from the reaction mixture with water at pH of 6–8 and at a temperature of 0–15° C.;
   e) transforming compound (III) into (6R,7R)-7-amino-3-carbamoyloxymethyl-ceph-3-em-4-carboxylic acid (IV)

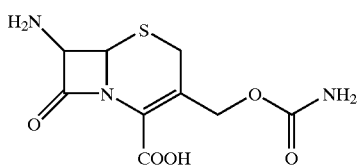

by glutaryl acylase enzymatic hydrolysis, at pH 7–9 and at a temperature of 20–30° C.;

f) condensing compound (IV) with a 2-furanyl(sin-methoxyimino)acetic acid halide or anhydride, to obtain the desired Cefuroxime acid (I).

2. A process as claimed in claim 1, in which said organic solvent is cyclohexanone.

3. A process as claimed in claim 2, in which said deacetyl 7-glutaryl ACA (II) aqueous solution has a concentration of 1–20%.

4. A process as claimed in claim 1, in which in step b) the organic phase is dried to a water content below 0.5%.

5. A process as claimed in claim 1, in which said activated isocyanate is chlorosulfonyl isocyanate.

6. A process as claimed in claim 1, in which said glutaryl acylase is supported on a macroreticular resin.

7. A process as claimed in claim 6, in which said resin is a polyacrylic epoxide resin.

8. A process as claimed in claim 7, in which said glutaryl acylase is isolated from an *Escherichia Coli* culture.

* * * * *